United States Patent
Duvert et al.

(10) Patent No.: US 7,175,851 B2
(45) Date of Patent: Feb. 13, 2007

(54) FUNGICIDAL COMPOSITION COMPRISING IN PARTICULAR AN OIL OF PLANT ORIGIN WITH HIGH SICCATIVE POWER

(75) Inventors: Patrice Duvert, Lyons (FR); Isabelle Martinon, Lyons (FR); Corinne Buiret, Lyons (FR)

(73) Assignee: Bayer Cropscience S.A. (FR)

( * ) Notice: Subject to any disclaimer, the term of this patent is extended or adjusted under 35 U.S.C. 154(b) by 238 days.

(21) Appl. No.: 10/332,718

(22) PCT Filed: Jul. 19, 2001

(86) PCT No.: PCT/FR01/02346

§ 371 (c)(1),
(2), (4) Date: Jan. 13, 2003

(87) PCT Pub. No.: WO02/09517

PCT Pub. Date: Feb. 7, 2002

(65) Prior Publication Data

US 2005/0019434 A1    Jan. 27, 2005

(30) Foreign Application Priority Data

Jul. 28, 2000    (FR) .................................. 00 09898

(51) Int. Cl.
*A01N 25/32*    (2006.01)
*A01N 43/54*    (2006.01)

(52) U.S. Cl. ..................... 424/406; 424/405; 514/398

(58) Field of Classification Search ................ 424/405, 424/406, 731, 750, 764, 768; 514/376, 398, 514/421

See application file for complete search history.

(56) References Cited

U.S. PATENT DOCUMENTS 4,761,423 A * 8/1988 Szego et al. ................. 514/395
5,580,567 A * 12/1996 Roberts ....................... 424/405

FOREIGN PATENT DOCUMENTS

| DE | 143547 | 9/1980 |
| DE | 3309765 | 9/1984 |
| EP | 0022666 | 1/1981 |
| FR | 2501966 | 9/1982 |
| FR | 2756464 | 6/1998 |
| JP | 56-008308 | 1/1981 |

OTHER PUBLICATIONS

Cu et al Adjuvants—pp. 657-666, 1992.*
White et al Plant disease 78 (I) 38-43, 1994.*
R.-O. Sarmiento, et al., "Control of Early Blight on Tomato and Net Spot on Cucumber Through Application of Sodium Bicarbonate and Vegetable Oil", *Horticultura brasileira*, vol. 17, No. 2, 1999, pp. 159-163.
S. Budavari (Ed.), et al., "*The Merck Index, Eleventh Edition*", Merck & Co., Rahway, N.J., p. 396, entry 2528 (Corn Oil); p. 867-868, entry 5386 (Linseed Oil); p. 1291-1292, entry 8127 (Rapeseed Oil); p. 1342, entry 8418 (Sesame Oil); p. 1376-1377, entry 8685 (Soybean Oil); p. p. 1422, entry 8982 (Sunflower Seed Oil), 1989.
R.J. Hamilton, "Structure and General Properties of Mineral and Vegetable Oils Used As Spray Adjuvants", *Pesticide Science*, G.B., Elsevier Applied Science Publisher, Barking, vol. 37, No. 2, 1993, pp. 141-146.
T.S. Thind, et al., "Use of Malathion and Stickers for Increasing the Efficacy of Fungicides for Controlling Purple Blotch of Onion", *Indian J. Agric. Sci.*, vol. 54, No. 4, 1984, pp. 299-302.
F.D. Smith, et al., "Use of Pinolene or Other Spray Adjuvants With Iprodione for Improved Control of Sclerotinia Blight on Peanut", *Peanut Science*, vol. 18, No. 2, 1991, pp. 97-101.
J.E. Adaskaveg, et al., "Postharvest Treatments With Iprodione Wax/Oil Mixtures for Control of Gray Mold and Other Decays of Strawberry", *Phytopathology*, vol. 84, No. 10, 1994, p. 1167.
R.M. Cu, et al., "Adjuvant Effects of Soyoil 937(R) on Fungicides for Control of Early Leafspot and Sclerotinia Blight in Peanuts", *Adjuvants for Agrichemicals, Paper Presented at the Second International Symposium on Adjuvants for Agrichemicals*, Blacksburg, VA., Jul. 31-Aug. 3, 1989, 1992, pp. 657-666.
T.B. Bhandari, et al., "Occurrence of Die-Back of Rose in Kumaon Hills and its Control", *Progressive Horticulture*, vol. 21, No. 3-4, 1989, pp. 341-342.
J.D. Mumford, "The Use of Soybean Oil With Pesticides in Western Europe", *Mededelinger van de Fuculteit Landbouwwetenschappen, Rijksuniversiteit Gent*, vol. 51, No. 2a, 1986, pp. 275-283.
G. Barnett, "The Increased Yield Response of Winter Wheat to Low Pesticide Programmes With A Vegetable Oil Based Carrier Adjuvant", *Mededelinger van de Fuculteit Landbouwwetenschappen, Rijksuniversiteit Gent*, vol. 55, No. 3b, 1990, pp. 1343-1347.

* cited by examiner

*Primary Examiner*—Neil S. Levy
(74) *Attorney, Agent, or Firm*—Ostrolenk, Faber, Gerb & Soffen, LLP

(57) ABSTRACT

The subject of the present invention is a fungicidal composition useful for the treatment of fungal diseases of crops and which comprises in particular at least one vegetable oil with high siccative power, as well as a method of treating crops using such a composition.

12 Claims, No Drawings

FUNGICIDAL COMPOSITION COMPRISING IN PARTICULAR AN OIL OF PLANT ORIGIN WITH HIGH SICCATIVE POWER

The subject of the present invention is a fungicidal composition useful for the treatment of fungal diseases of crops and which comprises a vegetable oil with high siccative power, and a method of treating crops using a composition according to the invention.

It is always desirable to reduce the doses of chemical products spread in the environment, for treating fungal diseases of crops, in particular by reducing the doses for application.

To do this, certain adjuvants, termed biological activators such as mineral oils, wetting agents and penetrating agents are combined with commercial proprietaries, and now make it possible, for example, to combine a mineral oil-type adjuvant with fungicidal compounds, which has the advantage of reducing the applied dose of fungicidal compounds. This thus broadens the possibilities of choices offered to farmers, so that the latter finds the solution best suited to their particular problem.

On the other hand, the use of some of these proprietaries is restricted when cases of phytotoxicity are observed on certain crops.

One aim of the invention is therefore to provide a novel fungicidal composition, allowing better selectivity even on so-called sensitive crops, while preserving an equivalent biological activity, preventively or curatively, against various diseases.

It has now been found that these aims could be achieved using the fungicidal composition according to the invention.

The subject of the present invention is a fungicidal composition useful for the treatment of fungal diseases of crops, based on at least one fungicidal compound and at least one adjuvant of the oil of plant origin type possessing high siccative power, the latter acting as activator (doping agent). It also relates to a method of treating crops with the same aim.

A fairly large number of examples of the use of vegetable oils in formulations of pesticidal, and in particular fungicidal, compounds, are known in the literature.

Nevertheless, no use of vegetable oils possessing high siccative power in fungicidal compositions has ever been reported.

Thus, and most surprisingly, such a use in fungicidal compositions according to the invention has made it possible to obtain particularly advantageous results.

The fungicidal compounds according to the present invention are, for the most part, known to farmers in particular for their efficacy against the diseases affecting or likely to affect cereals and other crops.

One advantage is also noted with regard to the use of certain vegetable oils which make it possible to reduce by 3 the dose of oil while preserving an equivalent biological efficacy.

Furthermore, the composition of the formulation proposed makes it possible to obtain an excellent physical quality of the plant-protection mixture for application and thus allows its use with various other commercial combinations with no risk of physicochemical incompatibility.

Such a stability of the plant-protection mixture for application of the fungicidal composition according to the invention also makes it possible to be able to formulate certain active substances which are otherwise difficult or even impossible to formulate.

Another aim of the invention is to provide a novel fungicidal combination useful in the preventive or curative treatment of diseases.

Another aim of the invention is to provide a fungicidal combination allowing improved efficacy, preventively or curatively, against various diseases and/or improved selectivity.

Another aim of the invention is to improve, in terms of persistance, the action of the fungicidal compounds.

Another aim is to provide combinations which allow better resistance to adverse weather conditions, in particular to rain.

Surprisingly, a fungicidal composition has now been found which provides complete or partial solutions to the problems and disadvantages which have just been mentioned.

The fungicidal composition according to the invention is characterized in that it comprises at least one fungicidal compound A and at least one oil B, this oil being of plant origin and possessing a high siccative power.

The advantages linked to the selective use of vegetable oils possessing a high siccative power are in particular their nontoxicity or at the very least a lower toxicity, compared with oils of mineral origin, a lower phytotoxicity, and greater biodegradability.

According to a very advantageous embodiment of the fungicidal composition according to the invention, the fungicidal compound A is chosen from dicarboximide derivatives.

Among these dicarboximide derivatives, those of the group comprising captan, captafol, chlozolinate, iprodione, procymidone and vinchlozolin are most particularly preferred.

Preferably, the fungicidal compound A is iprodione.

The invention therefore relates to a fungicidal composition combining an oily organic phase B which is a selection of unsaturated vegetable oil, of isomerized oil, of vegetable oil ester, of vegetable polymer and/or of a mixture of these various organic phases.

The vegetable oils may be of various origins, but those derived from linseed, sunflower, soya bean, maize, cotton, safflower and rapeseed will be preferred. These oils are available in various qualities, namely crude, refined or isomerized.

Preferably, the oil is a polyunsaturated vegetable oil which naturally contains a large number of unsaturations.

The expression polyunsaturated oil is understood to mean a triglyceride in which the majority of the linear fatty chains possess two or three double bonds per chain, noted C18:2 or C18:3, that is to say chains consisting of 18 carbon atoms with 2 or 3 unsaturations.

As examples of polyunsaturated oils, there may be mentioned triglycerides which predominantly contain so-called linoleic (C18:3) fatty acid chains such as linseed oil. As a guide, the composition by weight of this oil, characterized as fatty acids, may be within the following range: 50 to 60% of C18:3—10 to 17% of C18:2—15 to 25% of C18:1—2 to 4% of C18:0—5 to 8% of C16:0.

As an example of polyunsaturated oils, there may also be mentioned triglycerides predominantly containing fatty acid chains of the linoleic type (C18:2) such as sunflower, maize, soya bean, safflower, cotton or rapeseed oil. As a guide, the composition of these oils, characterized as fatty acids, may be within the following range: 45 to 70% of C18:2—0.1 to 10% of C18:3—10 to 40% of C18:1—0.1 to 10% of C18:0—1 to 26% of C16:0.

In other words, the oil coming within the scope of the present invention is said to be siccative. The siccativity is either natural (siccative or semi-siccative oils) or is obtained by chemical treatment of an oil which is not or not very siccative (so-called semisiccative or nonsiccative oils), this oil is then said to be isomerized.

The isomerization reaction consists in conjugating the double bonds in the fatty acid chain —CH=CH—CH2-CH=CH—, so as to obtain conjugated dienes as follows —CH=CH—CH=CH—CH2-, thus increasing their siccativity (reactivity to air).

There may be mentioned, as isomerized oil, isomerized sunflower oil with a percentage of conjugated dienes of between 16 and 18%, but also isomerized linseed oil containing 11 to 13% of conjugated dienes.

For the fungicidal composition according to the invention, the use of vegetable oils whose iodine value linked to their siccative power is greater than 70, preferably greater than 90, more preferably still greater than 130, most preferably greater than 150, is preferred.

The present invention also relates to a combination of compounds A and B, such a combination is then a combination of two compounds, and may be applied simultaneously as a ready-to-use mixture or as a freshly made mixture.

The compound B/compound A weight ratio in the composition according to the invention is generally between 0.15 and 1.6, preferably between 0.2 and 1.35, more preferably still between 0.25 and 1, or alternatively between 0.3 and 0.7, and most advantageously 0.45.

This composition is useful for the treatment of fungal diseases of various crops. It is thus effective for treating rust, leaf blotch, net blotch of barley; for treating eyespot, rust, septoria diseases, yellow leaf spot and fusaria of wheat. It is also effective for controlling grey mould, alternaria leaf spot, sclerotinia disease, net blotch and fusaria of protein-rich plants and of oil-producing plants (in particular pea, rapeseed and maize) and for the treatment of turf diseases such as rust, fusaria, sclerotinia and scurf.

It is particularly useful for the treatment of grey mould of vine, vegetable crops, the peach tree, the almond tree, the apple tree, the pear tree, the rape plant, the pea, the haricot bean and citrus; alternaria diseases of vegetable crops, the peach tree, the almond tree, the apple tree, the pear tree, the rape plant, potato and citrus; brown rot of the peach tree, the almond tree, the cherry tree; sclerotinia disease of vegetable crops, the rape plant and potato; and scurf of vegetable crops and rice.

Compounds A, contained in the composition according to the invention are described in at least one of the following manuals:

"The pesticide manual" edited by Clive TOMLIN and published by the British Crop Protection Council, 11th edition;

"1' Index phytosanitaire 2000", published by the Association de Coordination Technique Agricole, 36th edition.

Compound B, also contained in the composition according to the invention, is preferably refined and/or isomerized sunflower oil.

For their practical use, compounds A and B of the composition according to the invention are rarely used alone.

In the fungicidal composition according to the invention, compounds A and B most often represent from 0.5 to 95% by weight of the said composition as described above.

This may include the concentrated composition, that is to say the commercial product combining the two active substances (for the purposes of the present text, the expression active substance should be understood to mean both compound A, a fungicidal compound, and compound B, an adjuvant). This may also include the dilute composition ready to be sprayed on the crop to be treated. In the latter case, the dilution with water may be carried out either using a concentrated commercial composition containing the two active substances (this mixture is called "ready mix") or by means of the fresh mixture (called "tank mix") of two commercial concentrated compositions each containing one substance.

The composition according to the invention is liquid, and in this case in the form of a solution, suspension, emulsion or emulsifiable concentrate. Oil-aqueous liquid compositions are preferred both for their ease of use and the simplicity of their manufacture. Preferably, an aqueous concentrated suspension is available which uses vegetable oil in the form of an oil-in-water emulsion.

More generally, the composition according to the invention may include any solid or liquid additives corresponding to the customary techniques of formulating plant-protection products.

The composition according to the invention may comprise, in addition, any customary additives or adjuvants of plant-protection compositions, in particular carriers, surfactants, adhering agents, flow-enhancing agents and antigels. This composition may also contain any sort of other ingredients such as, for example, protective colloids, adhesives, thickeners, thixotropic agents, penetrating agents, stabilizers, sequestrants, pigments, colorants, polymers and antifoams.

The term "carrier" in the present text denotes a natural or synthetic, organic or inorganic material with which the active substances are combined to facilitate their application to the plant. This carrier is therefore generally inert and should be agriculturally acceptable, in particular on the treated plant. The carrier may be solid (clays, natural or synthetic silicates, silica, resins, waxes, solid fertilizers, and the like) or liquid (water, alcohols, ketones, petroleum fractions, aromatic or paraffin hydrocarbons, chlorinated hydrocarbons, liquefied gases and the like).

The surfactant may be an emulsifying, dispersing or wetting agent of the ionic or nonionic type. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (in particular alkylphenols or aryiphenols), salts of esters of sulphosuccinic acids, derivatives of taurine (in particular alkyl taurates), phosphoric esters of polyoxyethylated alcohols or phenols. The presence of at least one surfactant is desirable to promote the dispersion of the active substances in water and their good application to plants.

The expression oil-aqueous suspension concentrate is understood to mean an aqueous suspension in which the solid active substances are in the form of crystals in suspension in water and the oily organic phase, here the vegetable oil plus an emulsifier, in the form of an oil-in-water emulsion.

The suspension concentrates, which can also be applied by spraying, are prepared so as to obtain a stable fluid product which does not give rise to thickening or to the formation of a sediment after storage or to phase separation, and they usually contain from 10 to 75% of active substances, from 0.5 to 15% of surfactants, from 0.1 to 10% of thixotropic agents, from 0 to 10% of appropriate additives, such as pigments, colorants, antifoams, corrosion inhibitors, sterilizers, penetrating agents, adhesives and, as carrier, water or an organic liquid in which the active substances are not or not very soluble.

Some organic solid substances or inorganic salts may be dissolved or dispersed in the carrier to prevent sedimentation or as antigel for the water.

According to an advantageous variant of the invention and by way of example, here is a composition of the oil-aqueous suspension concentrate type:

EXAMPLE SC1

| Active substance | 375 |
|---|---|
| Ethoxylated polyararylphenol phosphate potassium salt | 60 |
| Dioctyl sulphosuccinate sodium salt | 10 |
| Ethoxylated oleic acid | 8.5 |
| Polyunsaturated vegetable oil | 170 |
| Monopropylene glycol | 50 |
| Polysaccharide | 1.4 |
| 1,2-Benzisothiazolin-3-one | 0.7 |
| Isotridecanol | 10 |
| Citric acid monohydrate | 1 |
| Water | (qs 1 liter) |

The composition according to the invention is prepared according to methods known per se. An example of a method, as a guide, is described below:

Add simultaneously, to water with stirring, monopropylene glycol, isotridecanol, ethoxylated polyararylphenol phosphate potassium salt, dioctyl sulphosuccinate sodium salt, citric acid monohydrate.

Continue stirring so as to disperse and dissolve the constituents.

Then add, with stirring, the active substance.

The suspension is pre-ground with the aid of a colloid mill and then ground to the final particle size with the aid of a ball mill.

With stirring, add the solution containing 2% of polysaccharide and 1% of 1,2-benzisothiazolin-3-one to the ground suspension.

With stirring, add the oily phase, consisting of the homogeneous mixture of vegetable oil and ethoxylated oleic acid, so as to form the oil-in-water emulsion.

The fungicidal composition which is the subject of the invention is applied by means of various methods of treatment such as spraying onto the aerial parts of the crops to be treated with a liquid comprising the said composition, sprinkling, injection into the trees and coating.

Spraying a liquid on the aerial parts of the crops to be treated is the preferred method of treatment.

The invention finally relates to a method of treatment intended for combating or preventing fungal diseases of crops, characterized in that an effective and non-phytotoxic dose of a composition according to the invention is applied to the aerial parts of the plants.

The expression "effective and non-phytotoxic quantity" is understood to mean a quantity of composition according to the invention sufficient to allow control or destruction of the fungi present or likely to appear on the crops, and resulting in no symptom of phytotoxicity for the said crops. Such a quantity is likely to vary within broad limits depending on the fungus to be combated, the type of crop, the climatic conditions and the compounds included in the fungicidal composition according to the invention. This quantity may be determined by systematic field trials, within the capability of persons skilled in the art.

These combinations are advantageously used so that the applied dose is between 250 and 1000 g/ha, preferably between 500 and 750 g/ha for compound A and between 0.25 to 0.45 times the dose of compound A, that is from 225 to 337.5 g/ha for a ratio of 0.45 P (P=guarantee in relation to active substance) for compound B (when A is taken at 1st preference doses of 500 to 750 g/ha).

These doses depend on the plant treated, the degree of infestation, the climatic conditions and the like. For example, in the case of turf, the dose of A may be up to 5 kg/ha.

Phytopathogenic fungi of crops which may be combated by this process are in particular those:

of the adelomycetes group:
of the genus *Alternaria*, for example *A. solani*, *A. citri*, *A. mali*, *A. kikuchiana*, *A. alternata*, *A. porri*, *A. brassicae*, *A. brassicicola*, *A. dauci*, and the like
of the genus *Botrytis*, for example *B. cinerea* or *B. squamosa*,
of the genus *Sclerotinia*, for example *S. sclerotinium*, *S. minor* or *S. homeocarpa*,
of the genus *Penicillium*, for example *P. digitatum*, *P. expansum*,
of the genus *Monilia*, for example *M. Mali*, *M. laxa*, *M. fructigena*,
of the genus *Rhizopus*, for example *R. stolonifer*,
of the genus *Sclerotium*, for example *S. cepivorum*,
of the genus *Fusarium*, for example *F. roseum*,
of the genus *Helminthosporium*, for example *H. allii*,
of the genus *Ascochyta*, for example *A. pisi*,
of the genus *Microdochium*, for example *M. nivale*,
of the *Basidiomycetes* group:
of the family *Rhizoctonia* spp.

A classification made, no longer based on the fungi targeted, but on the target crops may be illustrated as below:

barley: net blotch (*Helminthosporium*),
rapeseed: alternaria leaf spot (*Alternaria* spp.), grey mould (*Botrytis cinerea*), sclerotinia diseases (*Sclerotinia sclerotiorum*)
vine: grey mould (*Botrytis cinerea*),
Solanaceae: alternaria leaf spot (*Alternaria solani*) and grey mould (*Botrytis cinerea*) in particular,
vegetable crops: alternaria leaf spot (*Alternaria* spp.), sclerotinia diseases (*Sclerotinia* spp.), grey mould (*Botrytis cinerea*), foot or root rot (*Rhizoctonia* spp.),
rice: foot or root rot (*Rhizoctonia* spp.), decoloration of the grains (*Alternaria* spp., *Helminthosporium* spp., and the like),
arboriculture: alternaria leaf spot (*Alternaria* spp.), grey mould (*Botrytis cinerea*) and brown rot (*Monilia fructigena*),
citrus: scab (*Elsinoe fawcetti*), green and blue moulds (*Penicillium digitatum* and *P. expansum*),
turf: rust, oidium, net blotch, telluric diseases (*Microdochium nivale*, *Pythium* spp. *Rhizoctonia solani*, *Sclerotinia homeocarpa* and the like).

Among the crops suitable for the method of treatment according to the invention, there may be mentioned cereals, in particular barley, protein-rich plants and oil-producing plants, such as peas, rapeseed, sunflower, maize, vine, potato, tomato, vegetable crops (lettuce, Cucurbitaceae and the like), rice, arboriculture (apple tree, pear tree, cherry tree and the like), citrus and turf.

In the method of treatment according to the invention, components A and B of the composition according to the invention are generally applied simultaneously, by means of a composition according to the invention prepared from a ready-to-use concentrate or from a tank mix.

Another aspect of the invention relates to a product for applying simultaneously, sequentially or alternately compounds A and B of the fungicidal composition according to the invention.

The following examples are given without limitation of the advantageous properties of the combinations according to the invention.

The compositions, numbered with roman numerals, are of the type described above.

EXAMPLE 1

In this study, the effect of the nature of the vegetable or mineral oil is compared in terms of selectivity and efficacy, with or without rain, by means of two formulations, numbered in roman numerals, such as:
I: 255 g/l of iprodione+255 g/l of mineral oil SIB (that is to say Summer Insecticide Base) (SC).
II: 255 g/l of iprodione+255 g/l of vegetable oil Rapeseed CT (SC).

The experimental protocol relating to the study of the selectivity on tobacco plants is the following:

The two formulations are sprayed at doses of 750 and 1500 g of iprodione/ha in a plant-protection mixture volume of 150 /ha on 2-week old young tobacco plants (4-6 leaf stage) (3 repetitions/test factor). After drying of the products sprayed onto leaves, the plants are placed in a controlled environment cabinet at 25° C. during the day and 20° C. during the night (photoperiod 16 h/8 h). A phytotoxicity score (as % of surface attacked) is determined after 7 days (7 JAT1) followed by a second treatment and then the placing of the plants under the same conditions as above. A final phytotoxicity score is determined after 7 days (7 JAT2).

| | Selectivity | | 7 JAT1 | 7 JAT2 |
|---|---|---|---|---|
| I | 750 g/ha | 1 P SIB | 0.7 | 1.0 |
| | 1500 g/ha | mineral | 2.3 | 4.3 |
| II | 750 g/ha | 1 P Rapeseed CT | 1.0 | 1.0 |
| | 1500 g/ha | vegetable | 1.3 | 1.3 |

The formulation based on rapeseed vegetable oil is found to be more selective than the formulation based on mineral oil Summer Insecticide Base for the same dose of oil.

The efficacy is determined against *Botrytis cinerea* of gherkin in the presence or in the absence of washing out, that is to say with or without rain. For this study, the experimental protocol is the following:

The formulations under study are used at doses of 50–100–200 and 400 ppm of iprodione (test without washing out) or 100–200–400 and 800 ppm of iprodione (test with washing out). They are sprayed on gherkins, Petit Vert de Paris variety, at the cotyledon-first visible leaf stage (2×3 repeats/test factor). Four hours after the treatment, the groups of 3 plants/dose of fungicide under study are subjected to washing out with 25 mm of rain for 30 min. A day after the treatment, the gherkin plants are contaminated by depositing drops of water containing an inoculum at 150000 spores of *Botrytis cinerea*/ml of inoculum. They are then placed in a controlled environment cabinet at 12–15° C., 100% RH. A score (in % of surface attacked) is determined 7 days after the inoculation. The data then serve to establish a sigmoid type dose-response curve which makes it possible to determine the IC90 (concentration causing 90% inhibition of the disease) as well as the confidence interval in which each IC90 exists.

| | Efficacy and resistance to rain | | IC90 | min. IC | max. IC |
|---|---|---|---|---|---|
| I | | 1 P SIB | | | |
| without rain | | mineral | 137 | 96 | 194 |
| with rain | | | 459 | 383 | 550 |
| II | | 1 P Rapeseed | | | |
| without rain | | CT | 228 | 188 | 273 |
| | | vegetable | | | |
| with rain | | | 473 | 387 | 572 |

The formulation based on rapeseed vegetable oil has efficacy without rain which is slightly less than that based on mineral oil SIB, but with a nonsignificant difference in efficacy.

On the other hand, this formulation based on rapeseed oil exhibits efficacy in the presence of washing out with rain which is equivalent to the formulation containing the same dose of mineral oil SIB.

EXAMPLE 2

In this study, the effect of the nature of the vegetable or mineral oil is compared in terms of efficacy in the presence of rain (resistance to rain), by means of two formulations such as:
III: 255 g/l of iprodione+350 g/l of mineral oil SIB (SC).
IV: 500 g/l of iprodione+125 g/l of linseed oil TS (SC).

The efficacy is determined against *Botrytis cineria* of gherkin in the presence of rain. For this study, the experimental protocol is the same as above.

| | Resistance to rain | IC90 | min. IC | max. IC |
|---|---|---|---|---|
| III | 1.35 P SIB | 80 | 593 | 109 |
| with rain | mineral | 5 | | 3 |
| IV | 0.25 P | 96 | 915 | 101 |
| with rain | linseed TS | 2 | | 2 |

The linseed vegetable oil-based formulation appears slightly less effective than that based on mineral oil but this difference is not significant. This linseed vegetable oil-based formulation therefore exhibits efficacy in the presence of rain (resistance to washing out) equivalent to the formulation containing 1.35 P of mineral oil. It should be noted that the dose of vegetable oil used is about 5 times less than that used in III (for an equal dose of active substance).

EXAMPLE 3

In this study, the effect of the nature of the vegetable or mineral oil is compared in terms of efficacy in the presence of rain (resistance to rain), by means of four formulations such as:
V: 500 g/l of iprodione+175 g/l of linseed oil TS (SC).
VI: 500 g/l of iprodione+175 g/l of refined sunflower oil (SC).
VII: 500 g/l of iprodione+175 g/l of mineral oil SIB (SC).
III: 255 g/l of iprodione+350 g/l of mineral oil SIB (SC).

The efficacy is determined against *Botrytis cineria* of gherkin in the presence of washing out with rain. For this study, the experimental protocol is the same as above.

| | Resistance to rain | IC90 | min. IC | max. IC |
|---|---|---|---|---|
| V | 0.35 P linseed | 327 | 262 | 407 |
| VI | 0.35 P refined sunflower | 287 | 252 | 330 |
| VII | 0.35 P SIB mineral | 497 | 445 | 555 |
| III | 1.35 P SIB mineral | 290 | 225 | 372 |

The two vegetable oil-based formulations containing only 0.35 P of oil exhibit resistance to rain equivalent to that of III (formulation containing 3.8 times more mineral oil).

The mineral oil-based formulation at the dose of 0.35 P is found to be significantly less resistant to rain than those containing the same dose of polyunsaturated vegetable oil such as refined sunflower or linseed oil.

EXAMPLE 4

In this study, the effect of the nature of the vegetable or mineral oil is compared in terms of efficacy, resistance to rain and selectivity, by means of three formulations such as:

VIII: 500 g/l of iprodione+175 g/l of isomerized sunflower oil (SC).

IX: 500 g/l of iprodione without addition of oil (SC).

III: 255 g/l of iprodione+350 g/l of mineral oil SIB (SC).

The efficacy is determined against *Botrytis cineria* of gherkin in the presence or absence of washing out with rain. For this study, the experimental protocol is the same as above.

| | Efficacy and resistance to rain | | IC90 | min. IC | max. IC |
|---|---|---|---|---|---|
| VIII | without rain | 0.35 P | 165 | 106 | 257 |
| | with rain | isomerized sunflower | 509 | 397 | 653 |
| IX | without rain | without oil | 168 | 95 | 297 |
| | with rain | | 954 | 702 | 1297 |
| III | without rain | 1.35 P SIB | 162 | 108 | 242 |
| | with rain | | 487 | 428 | 555 |

The formulation containing an isomerized sun-flower vegetable oil exhibits efficacy without rain and resistance to rain equivalent to III. The use of a vegetable oil of this type, that is to say polyunsaturated, makes it possible to reduce the dose of oil by about 3.8 fold, in the treatment plant-protection mixture.

The selectivity is determined on tobacco plants according to the protocol previously described:

| | Selectivity | | 7 JAT1 | 7 JAT2 |
|---|---|---|---|---|
| VIII | 750 g/ha | 0.35 P isomerized sunflower | 0 | 1.7 |
| | 1500 g/ha | | 0 | 2.0 |
| IX | 750 g/ha | without oil | 0.7 | 1.0 |
| IX | 1500 g/ha | | 0.3 | 0.3 |
| III | 750 g/ha | 1.35 P SIB | 1.3 | 1.3 |
| III | 1500 g/ha | | 13.0 | 15.0 |

From the first application, the mineral oil-based formulation exhibits unacceptable phytotoxicity. On the other hand, the isomerized sunflower vegetable oil-based formulation is found to be particularly selective on tobacco plants.

EXAMPLE 5

In this study, the effect of the nature of the vegetable or mineral oil, and the effect of the dose of vegetable oil are compared in terms of efficacy, resistance to washing out and selectivity by means of five formulations such as:

X: 375 g of iprodione/l+131 g/l of refined sunflower oil (SC).

XI: 375 g of iprodione/l+169 g/l of refined sunflower oil (SC).

XII: 375 g of iprodione/l+206 g/l of refined sunflower oil (SC).

IX: 500 g of iprodione/l without addition of oil (SC).

III: 255 g of iprodione/l+350 g/l of mineral oil SIB (SC).

The efficacy is determined against *Botrytis cinerea* of gherkin in the presence or the absence of rain. For this study, the experimental protocol is the same as above.

| | Efficacy and resistance to washing out | | IC90 | min. IC | max. IC |
|---|---|---|---|---|---|
| X | without rain | 0.35 P | 150 | 107 | 212 |
| | with rain | refined sunflower | 512 | 492 | 533 |
| XI | without rain | 0.45 P | 135 | 111 | 165 |
| | with rain | refined sunflower | 479 | 439 | 522 |
| XII | without rain | 0.55 P | 142 | 120 | 169 |
| | with rain | refined sunflower | 426 | 379 | 480 |
| IX | without rain | without oil | 139 | 95 | 202 |
| | with rain | | 838 | 621 | 1129 |
| III | without rain | 1.35 P SIB | 205 | 137 | 307 |
| | with rain | | 532 | 425 | 666 |

The formulations containing a refined sunflower vegetable oil at doses of 0.35 P, 0.45 P and 0.55 P exhibit efficacy without rain and resistance to rain equivalent to those of III. The use of a highly polyunsaturated vegetable oil makes it possible to reduce the dose of oil to about 3.8 fold in the treatment plant-protection mixture.

The selectivity is determined on tobacco plants for these five formulations as well as the following formulation:

XIII: SC containing 375 g of iprodione/l+199 g/l of mineral oil SIB.

This formulation makes it possible to determine the effect of the dose of mineral oil on the selectivity of the product.

The protocol remains the same as previously described:

| Selectivity | | | 7 JAT1 | 7 JAT2 |
|---|---|---|---|---|
| X | 750 g/ha | 0.35 P | 0.3 | 1.0 |
| | 1500 g/ha | refined sunflower | 0.3 | 0 |
| XI | 750 g/ha | 0.45 P | 0.7 | 1.0 |
| | 1500 g/ha | refined sunflower | 1.3 | 0.7 |
| XII | 750 g/ha | 0.55 P | 0.7 | 0.3 |
| | 1500 g/ha | refined sunflower | 0.7 | 1.3 |
| IX | 750 g/ha | without oil | 0.3 | 0 |
| | 1500 g/ha | | 0 | 0 |
| XIII | 750 g/ha | 0.53 P SIB | 1.0 | 0.3 |
| | 1500 g/ha | | 2.3 | 2.3 |
| III | 750 g/ha | 1.35 P SIB | 2.7 | 2.3 |
| | 1500 g/ha | | 3.3 | 6.0 |

The refined sunflower vegetable oil-based formulations exhibit better selectivity than that of III. The incorporation of mineral oil leads to phytotoxicity which is sometimes unacceptable which is found to be dose-dependent.

EXAMPLE 6

In this study, the effect of the nature of the vegetable or mineral oil is compared in terms of efficacy, resistance to washing out and selectivity by means of three formulations such as:

XIV: 375 g/l of iprodione+170 g/l of refined sunflower oil (SC).

IX: 500 g/l of iprodione without addition of oil (SC).

III: 255 g/l of iprodione+350 g/l of mineral oil SIB (SC).

The efficacy is determined against *Botrytis cinerea* of gherkin in the presence or in the absence of washing out with rain. For this study, the experimental protocol is the same as above.

| Efficacy and resistance to rain | | | IC90 | min. IC | max. IC |
|---|---|---|---|---|---|
| XIV | without rain | 0.45 P | 122 | 83 | 178 |
| | with rain | refined sunflower | 446 | 392 | 513 |
| IX | without rain | without oil | 114 | 97 | 134 |
| | with rain | | 671 | 518 | 880 |
| III | without rain | 1.35 SIB | 116 | 104 | 129 |
| III | with rain | mineral | 509 | 411 | 630 |

The formulation containing the refined sunflower vegetable oil exhibits efficacy without rain and resistance to rain equivalent to that of III. The use of a vegetable oil of this type, that is to say polyunsaturated, makes it possible to reduce the dose of oil by 3, in the treatment plantprotection mixture.

The selectivity is determined on tobacco plants according to the protocol previously described:

| Selectivity | | | 7 JAT1 | 7 JAT2 |
|---|---|---|---|---|
| XIV | 750 g/ha | 0.45 P | 1.7 | 1.7 |
| | 1500 g/ha | refined sunflower | 4.7 | 3.7 |
| IX | 750 g/ha | without oil | 0.3 | 0.3 |
| | 1500 g/ha | | 1.3 | 0.3 |
| III | 750 g/ha | 1.35 P SIB | 3.3 | 1.3 |
| | 1500 g/ha | mineral | 16.7 | 16.7 |

From the first application, the mineral oil-based formulation exhibits unacceptable phytotoxicity. On the other hand, the vegetable oil-based formulation containing 0.45 P of refined sunflower is found to be particularly more selective than III.

GENERAL CONCLUSION

These polyunsaturated vegetable oil-based formulations therefore favourably meet the object set. Indeed, the formulations based on vegetable oils exhibit better selectivity than the formulation based on mineral oil (Summer Insecticide Base), the biological activity, with or without washing out, is at the same level as that of the most effective mineral oil-based Summer Insecticide Base formulations.

The advantage of this type of suspension concentrates also consists in the use of a dose of oil which is three times less, in the treatment plant-protection mixture, than that customarily used in the case of the mineral oil SIB.

The invention claimed is:

1. A fungicidal composition consisting essentially of at least one fungicidal compound A, iprodione, and at least one oil B, this oil being of plant origin and possessing a high siccative power selected from the group consisting of linseed, sunflower, soya bean, maize, cottonseed, safflower and rapeseed oils, and possessing an iodine value greater than 90, wherein the compound B/compound A weight ratio is between 0.15 and 1.6.

2. The fungicidal composition of claim 1 wherein the compound B/compound A weight ratio is 0.45.

3. The fungicidal composition of claim 1 wherein compounds A and B represent from 0.5 to 95% by weight of the said composition.

4. A method of treatment for combating fungal diseases of crops comprising applying an effective and non-phytotoxic dose of the composition of claim 1 to the aerial parts of the plants.

5. The method of claim 4 wherein the crops are selected from the group consisting of cereals, protein-rich plants, oil-producing plants, peas, rapeseed, sunflower, maize, vine, potato, tomato, vegetable crops, rice, arboriculture, citrus and turf.

6. The method of treatment of claim 4 wherein a dose of between 250 and 1000 g/ha of compound A and between 0.25 and 0.45 times the dose of compound A of compound B is applied.

7. A fungicidal composition consisting essentially of:
(i) at least one fungicidal compound A, said fungicidal compound A being iprodione; and
(ii) at least one oil B, said oil B being of plant origin, possessing a high siccative power, and possessing an iodine value greater than 150, wherein the compound B/compound A weight ratio is between 0.15 and 1.6.

8. A method of treatment for combating fungal diseases of crops comprising applying an effective and non-phytotoxic dose of the composition of claim 7 to the aerial parts of the plants.

9. A fungicidal composition consisting essentially of:
   (i) at least one fungicidal compound A, said fungicidal compound A being iprodione; and
   (ii) at least one oil B, said oil B being sunflower oil and possessing a high siccative power, wherein the compound B/compound A weight ratio is between 0.15 and 1.6.

10. A method of treatment for combating fungal diseases of crops comprising applying an effective and non-phytotoxic dose of the composition of claim 9 to the aerial parts of the plants.

11. A fungicidal composition consisting essentially of:
    (i) at least one fungicidal compound A, said fungicidal compound A being iprodione; and
    (ii) at least one oil B selected from the group consisting of linseed, sunflower, soya bean, maize, cottonseed, safflower and rapeseed oils, said oil possessing a high siccative power, wherein the compound B/compound A weight ratio is 0.45.

12. A method of treatment for combating fungal diseases of crops comprising applying an effective and non-phytotoxic dose of the composition of claim 11 to the aerial parts of the plants.

* * * * *

UNITED STATES PATENT AND TRADEMARK OFFICE
CERTIFICATE OF CORRECTION

PATENT NO. : 7,175,851 B2  Page 1 of 1
APPLICATION NO. : 10/332718
DATED : February 13, 2007
INVENTOR(S) : Duvert et al.

It is certified that error appears in the above-identified patent and that said Letters Patent is hereby corrected as shown below:

On the title page item (75), should read as follows:

(75) Inventors: Patrice Duvert, Lyon (FR); Isabelle Martinon, Lyon (FR); Corinne Buiret, Lyon (FR)

Signed and Sealed this

Twenty-sixth Day of August, 2008

JON W. DUDAS
*Director of the United States Patent and Trademark Office*